(12) United States Patent
Okada et al.

(10) Patent No.: US 7,914,790 B2
(45) Date of Patent: Mar. 29, 2011

(54) HUMAN IGM ANTIBODY LYSING ACTIVATED LYMPHOCYTES UNDER MEDIATION BY HOMOLOGOUS COMPLEMENT

(76) Inventors: Hidechika Okada, Nagoya (JP); Noriko Okada, Nagoya (JP)

( * ) Notice: Subject to any disclaimer, the term of this patent is extended or adjusted under 35 U.S.C. 154(b) by 1560 days.

(21) Appl. No.: 10/520,016

(22) PCT Filed: Jun. 30, 2003

(86) PCT No.: PCT/JP03/08306
§ 371 (c)(1),
(2), (4) Date: Oct. 20, 2005

(87) PCT Pub. No.: WO2004/003196
PCT Pub. Date: Jan. 8, 2004

(65) Prior Publication Data
US 2006/0140964 A1    Jun. 29, 2006

(30) Foreign Application Priority Data

Jul. 1, 2002 (JP) .................................. 2002-227952
Mar. 18, 2003 (JP) ................................. 2003-074312

(51) Int. Cl.
*A61K 39/395* (2006.01)
*C12N 5/07* (2006.01)
(52) U.S. Cl. ................... 424/154.1; 435/343.2; 530/809

(58) Field of Classification Search .................. None
See application file for complete search history.

(56) References Cited

FOREIGN PATENT DOCUMENTS
WO       WO97/22361       6/1997

OTHER PUBLICATIONS

Noriko Okada et al., "Human IgM Monoclonal Antibodies Reactive with HIV-1-Infected Cells Generated Using a Trans-Chromosome Mouse", Microbiol. Immunol., 2005, 49(5): 447-459.

*Primary Examiner* — Zachariah Lucas
*Assistant Examiner* — Nicole Kinsey White
(74) *Attorney, Agent, or Firm* — Sughrue Mion, PLLC (57) ABSTRACT

A human IgM monoclonal antibody responding to HIV-infected cells too, which is characterized by lysing activated human lymphocytes, etc. under the mediation by a homologous human complement, is obtained. Using the thus obtained monoclonal antibody, it is intended to provide an immune reaction controlling remedy, etc. containing the human IgM monoclonal antibody which responds specifically to activated lymphocytes and induces cell lysis under the mediation by a homologous complement. Using the human IgM monoclonal antibody responding to activated human lymphocytes, it is also intended to provide an HIV remedy, etc. characterized by lysing and eliminating activated lymphocytes to thereby treat transplantation rejection and autoimmune diseases caused by an over-response of T lymphocytes as well as HIV infection.

3 Claims, 4 Drawing Sheets

FIG. 4 schematic diagram of 9F11 μ-chain plasmid construct

SEQUENCE LISTING

<160> NUMBER OF SEQ ID NOS: 8

<210> SEQ ID NO 1
<211> LENGTH: 481
<212> TYPE: DNA
<213> ORGANISM: Artificial Sequence
<220> FEATURE:
<223> OTHER INFORMATION: Synthetic polynucleotide

<400> SEQUENCE: 1

| | | | | | |
|---|---|---|---|---|---|
| gctgaattct | ggctgaccag | ggcagtcacc | agagctccag | acaatgtctg | tctccttcct | 60 |
| catcttcctg | cccgtgctgg | gcctcccatg | gggtgtcctg | tcacaggtac | agctgcagca | 120 |
| gtcaggtcca | ggactggtga | agcccgcgca | gaccctctca | ctcacctgtg | ccatctccgg | 180 |
| ggacagtgtc | tctagcaaca | gtgctacttg | gaactggatc | aggcagtccc | cattgagagg | 240 |

```
ccttgagtgg ctgggaagga catactacag gtccaagtgg tataatgatt atgcagtatc    300
tgtgaaaagt cgaataacca tcaacccaga cacatccaag aaccagttct ccctgcagct    360
gaactctgtg actcccgagg acacggctgt gtattactgt gcaagagaga attactatgg    420 ttcgggggagg tacaactggt tcgacccctg gggccaggga accctggtca ccgtctcctc    480
a                                                                    481

<210> SEQ ID NO 2
<211> LENGTH: 401
<212> TYPE: DNA
<213> ORGANISM: Artificial Sequence
<220> FEATURE:
<223> OTHER INFORMATION: Synthetic polynucleotide

<400> SEQUENCE: 2
tgtcaggaca cagcatggac atgagggtcc ccgctcagct cctggggctc ctgctgctct     60
ggttcccagg ttccagatgc gacatccaga tgacccagtc tccatcttcc gtgtctgcat    120
ctgtaggaga cagagtcacc atcacttgtc gggcgagtca gggtattagc agctggttag    180
cctggtatca gcagaaacca gggaaagccc ctaagctcct gatctatgat gcatccagtt    240
tgcaaagtgg ggtcccatca aggttcagcg gcagtggatc tgggacagat ttcactctca    300
ccatcagcag cctgcagcct gaagattttg caacttacta ttgtcaacag gctaacagtt    360
tccctctcac tttcggcgga gggaccaagg tggagatcaa a                        401

<210> SEQ ID NO 3
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 3
atatctgttt cttttttaat tttttacct gtttaggtt taccttgagg tgttttatct       60
caagttcaat tacaacaatc tggtcctggt ttagttaaac ctgctcaaac tttatcttta    120
acttgtgcta tttctggtga ttctgtttct tctaattctg ctacttgaaa ttgaattcgt    180
caatctcctt tacgtggttt agaatgatta ggtcgtactt attatcgttc taaatgatat    240
aatgattatg ctgtttctgt taaatctcgt attactatta atcctgatac ttctaaaaat    300
caattttctt tacaattaaa ttctgttact cctgaagata ctgctgttta ttattgtgct    360
cgtgaaaatt attatggttc tggtcgttat aattgatttg atccttgagg tcaaggtact    420
ttagttactg tttcttct                                                  438

<210> SEQ ID NO 4
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 4
atgtccgtct ccttcttgat cttcttgccg gtcttgggct tgccctgggg cgtcttgtcc     60
caggtccagt tgcagcagtc cggccccggc ttggtcaagc cgcccagac cttgtccttg    120 acctgcgcca tctccggcga ctccgtctcc tccaactccg ccacctggaa ctggatccgc    180
cagtcccccc tgcgcggctt ggagtggttg ggccgcacct actaccgctc caagtggtac    240
aacgactacg ccgtctccgt caagtcccgc atcaccatca accccgacac ctccaagaac    300
```

```
cagttctcct tgcagttgaa ctccgtcacc cccgaggaca ccgccgtcta ctactgcgcc    360
cgcgagaact actacggctc cggccgctac aactggttcg acccctgggg ccagggcacc    420
ttggtcaccg tctcctcc                                                  438
```

```
<210> SEQ ID NO 5
<211> LENGTH: 121
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (110)..(119)
<220> FEATURE:
<221> NAME/KEY: misc_feature
<222> LOCATION: (110)..(119)
<223> OTHER INFORMATION: n is a, c, g, or t

<400> SEQUENCE: 5
```

```
aattccccac catggaactg gggctccgct gggttttcct tgttgctatt ttagaaggtg    60
tccagtgtga ggtgcagctg gtggagtctg ggggaggcct ggtcaagccn nnnnnnnng    120 g                                                                    121
```

```
<210> SEQ ID NO 6
<211> LENGTH: 121
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (106)..(115)
<223> OTHER INFORMATION: n is a, c, g, or t

<400> SEQUENCE: 6
```

```
ggggtggtac cttgaccccg aggcgaccca aaaggaacaa cgataaaatc ttccacaggt    60
cacactccac gtcgaccacc tcagaccccc tccggaccag ttcggnnnnn nnnnncctta    120
a                                                                    121
```

```
<210> SEQ ID NO 7
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 7
```

Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ala Gln Thr Leu Ser Leu Thr Cys Ala Ile Ser Gly Asp Ser
        35                  40                  45

Val Ser Ser Asn Ser Ala Thr Trp Asn Trp Ile Arg Gln Ser Pro Leu
    50                  55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

-continued

```
Asp Thr Ala Val Tyr Tyr Cys Ala Arg Glu Asn Tyr Tyr Gly Ser Gly
        115                 120                 125

Arg Tyr Asn Trp Phe Asp Pro Trp Gly Gln Gly Thr Leu Val Thr Val
    130                 135                 140

Ser Ser
145

<210> SEQ ID NO 8
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 8

Met Ser Val Ser Phe Leu Ile Phe Leu Pro Val Leu Gly Leu Pro Trp
1               5                   10                  15

Gly Val Leu Ser Gln Val Gln Leu
            20
```

HUMAN IGM ANTIBODY LYSING ACTIVATED LYMPHOCYTES UNDER MEDIATION BY HOMOLOGOUS COMPLEMENT

TECHNICAL FIELD

The invention relates to a human IgM monoclonal antibody reactive to HIV-infected cells that lyses activated lymphocytes by reacting with a differentiated antigen of the activated lymphocytes under medication by homologous human complements, and a remedy for autoimmune diseases containing the monoclonal antibody.

BACKGROUND ART

Various immunosuppressants such as cyclosporin and FK506 have been developed for controlling biological immunoreactions in collagen diseases, autoimmune diseases and rejection for organ transplantation. However, since such immunosuppressants are reactive to cells other than immunocompetent cells, side effects of these agent should be taken into consideration.

Various methods have been investigated for using antibodies that specifically react with target cells. For example, the target cell with which the antibody has reacted is expected to be lysed by reacting with a complement. While there are species-specific complement control membrane factors (such as DAF, decay accelerating factor; MCP, membrane cofactor protein; and HRF20, 20 kDa homologous restriction factor) on human cell membranes, they can induce no cytolysis reaction via complement reactions for preventing reactions among homologous human complements.

On the other hand, it was found that IgM antibodies in human serum that react with the HIV-infected cells are able to yield the cytolysis reaction of the HIV-infected cells via the human complement by overcoming the complement control membrane factors. It was revealed that the IgM antibody can exhibit such action as described above against gangliosides such as GM2 and Gg4 whose expression is enhanced by HIV-infection (Japanese Patent Application Laid-Open No. 9-227409).

L55 has been reported as the human IgM monoclonal antibody against GM2 of the gangliosides, wherein L55 is produced by immortalizing human B lymphoblast strain with EB virus. The HIV-infected cells after treating with this human IgM monoclonal antibody have been found to yield cytolysis via a reaction with the human complement.

DISCLOSURE OF INVENTION

An object of the invention is to provides a remedy for controlling immunological response containing a human IgM monoclonal antibody that specifically reacts with activated lymphocytes to induce cytolysis under mediation by homologous complements.

As a result of intensive studies for solving the problems above, the invention provides a human IgM monoclonal antibody reactive to HIV-infected cells that lyse activated human lymphocytes under mediation by homologous human complements.

The invention for solving the problems above provides an HIV remedy that cures transplantation rejection response and autoimmune diseases caused by excessive response of T-lymphocytes as well as HIV infection diseases by eliminating activated lymphocytes by cytolyses using a human IgM monoclonal antibody that reacts with HIV-infected cells and activated lymphocytes.

More specifically, the invention for solving the problems above provides the human IgM monoclonal antibody according to any one of first to second aspects, wherein the human IgM monoclonal antibody that reacts with the activated lymphocytes and the HIV-infected cells is 9F11 antibody having a base sequence of the H-chain variable region represented by sequence number 1.

More specifically, the invention for solving the problems above provides the human IgM monoclonal antibody according to any one of first to third aspects, wherein the human IgM monoclonal antibody that reacts with the activated lymphocytes and the HIV-infected cells is 9F11 antibody having a base sequence of the L-chain variable region represented by sequence number 2.

BRIEF DESCRIPTION OF THE DRAWINGS

The result of flow cytometory analysis shows that HIV-infected cells are stained with 9F11 antibodies while non-infected cells are not.

The drawing shows that 9F11 antibody reacts with the activated lymphocytes stimulated with PHA while it does not react with normal peripheral blood lymphocytes (PBMC: peripheral blood lymphocyte).

(A) Almost all cells are destroyed 4 hours after addition of 2 μg/ml of 9F11 antibody and fresh human serum (including a complement component) to HIV-1 infected cells MOLT-4/ IIIB. No effects have been observed at all when the serum is not added or on non-infected cells MOLT-4.

(B) 9F11 antigen is induced by activating the peripheral blood lymphocytes using PHA, and the cells are impaired by 9F11 antibody and the complement as in the HIV-1 infected cells (FHS: fresh human serum (used as a complement source), PHA: human lymphocyte activating agent, % $^{51}$Cr release=mortality of cells, PBMC: peripheral blood lymphocyte).

BEST MODE FOR CARRYING OUT THE INVENTION

While the invention is described in detail with reference to examples, the technical scope of the invention is by no means restricted to these examples.

For solving the problems above, the inventors of the invention immunized HIV-infected cells of a mouse (TC mouse: trans-chromosome mouse; prepared by Kirin Brewery Co., Ltd.) into which human immunoglobulin gene-containing chromosomes had been introduced, and obtained a mouse that produces human antibodies that specifically react with HIV-infected cells. Hybridoma was prepared by a conventional method by fusing spleen cells of the immunized mouse with a mouse myeloma cell strain. Clones producing the monoclonal antibody that react with the HIV-infected cells and lead the infected cells to cytolysis in the presence of a human complement were selected from the hybridoma. The selected hybridomas were named as 9F11 cell strain. A 9F11 antibody that is a monoclonal antibody produced by 9F11 cell strain is a human IgM monoclonal antibody comprising human μ-chain and human κ-chain. While 9F11 antibody was able to yield cytolysis by reacting with the HIV-infected cells under mediation by the human complement, the antibody also caused cytolysis for activated lymphocytes of non-infected lymphocytes. Accordingly, the response to the HIV-infected cells may be comprehended that the lymphocyte is brought to a certain kind of activated state by HIV infection, and the HIV-infected cells are lysed under mediation by the human complement by expressing an antigen (9F11 antigen) against 9F11 as a differentiated antigen. In other words, 9F11 antigen is a differentiated antigen that is expressed by activation of the lymphocyte, and 9F11 antibody that induces cytolysis under mediation by the complement by reacting with the antigen specifically leads the activated lymphocyte to cytolysis under mediation by the complement. It was therefore made clear that a remedy containing 9F11 antibody can be utilized in the treatment for suppressing the activated lymphocyte. The invention has been completed based on the discoveries described above. The cell strain 9F11 that produces 9F11 antibodies of the invention was deposited with National Institute of Advanced Industrial Science and Technology, International Patent Organism Depository (Chuo-6, Higashi 1-1-1, Tsukuba City, Ibaraki Pref.), on May 8, 2003, with an accession number of FERM BP-8379.

Table 1 shows the results of base sequence analysis of the genes in the variable regions in κ-chain and μ-chain, respectively, encoding 9F11 antibody. The base sequence of the constant region is approximately the same as the base sequence of reported genes.

TABLE 1

Base Sequence of ti-Chain Variable Region

GCTGAATTCTGGCTGACCAGGGCAGTCACCAGAGC  SEQ ID NO: 1

TCCAGACAATGTCTGTCTCCTTCCTCATCTTCCTG

CCCGTGCTGGGCCTCCCATGGGGTGTCCTGTCACA

GGTACAGCTGCAGCAGTCAGGTCCAGGACTGGTGA

AGCCCGCGCAGACCCTCTCACTCACCTGTGCCATC

TCCGGGGACAGTGTCTCTAGCAACAGTGCTACTTG

GAACTGGATCAGGCAGTCCCCATTGAGAGGCCTTG

AGTGGCTGGGAAGGACATACTACAGGTCCAAGTGG

TATAATGATTATGCAGTATCTGTGAAAAGTCGAAT

AACCATCAACCCAGACACATCCAAGAACCAGTTCT

CCCTGCAGCTGAACTCTGTGACTCCCCGAGGACAC

GGCTGTGTATTACTGTGCAAGAGAGAATTACTATG

GTTCGGGGAGGTACAACTGGTTCGACCCCTGGGGC

CAGGGAACCCTGGTCACCGTCTCCTCA

Base Sequence of is-Chain Variable Region

TGTCAGGACACAGCATGGACATGAGGGTCCCCGCT  SEQ ID NO: 2

CAGCTCCTGGGGCTCCTGCTGCTCTGGTTCCCAGG

TTCCAGATGCGACATCCAGATGACCCAGTCTCCAT

CTTCCGTGTCTGCATCTGTAGGAGACAGAGTCACC

ATCACTTGTCGGGCGAGTCAGGGTATTAGCAGCTG

GTTAGCCTGGTATCAGCAGAAACCAGGGAAAGCCC

CTAAGCTCCTGATCTATGATGCATCCAGTTTGCAA

AGTGGGGTCCCATCAAGGTTCAGCGGCAGTGGATC

TGGGACAGATTTCACTCTCACCATCAGCAGCCTGC

AGCCTGAAGATTTTGCAACTTACTATTGTCAACAG

TABLE 1-continued

GCTAACAGTTTCCCTCTCACTTTCGGCGGAGGGAC

CAAGGTGGAGATCAAA

The composition of the invention, which is used for an immunological reaction control agent containing the human IgM monoclonal antibody that specifically reacts with the activated lymphocytes and induces cytolysis under mediation by the homologous complement, may be obtained by combining with physiologically acceptable carriers. The physiologically acceptable carrier is known in the art, and includes physiological buffered saline or other aqueous solutions having a buffer action, or solvents such as glycols, glycerol, oils (for example olive oil) or injectable organic esters. The physiologically acceptable carrier may include compounds that stabilize human IgM antibody or enhance absorption thereof. Examples of the physiologically acceptable compounds include sugars such as glucose, sucrose and dextran; antioxidants such as ascorbic acid and glutathione; chelating agents; proteins such as albumin; and other stabilizers and excipients. Various immunosuppressants such as cyclosporin and FK506 as well as other immunosuppressants may be added to the composition. Any combinations of the physiologically acceptable carriers may be selected depending on administration path and disease of object.

Example 1

Specificity of 9F11 Antibody

Figure 1:
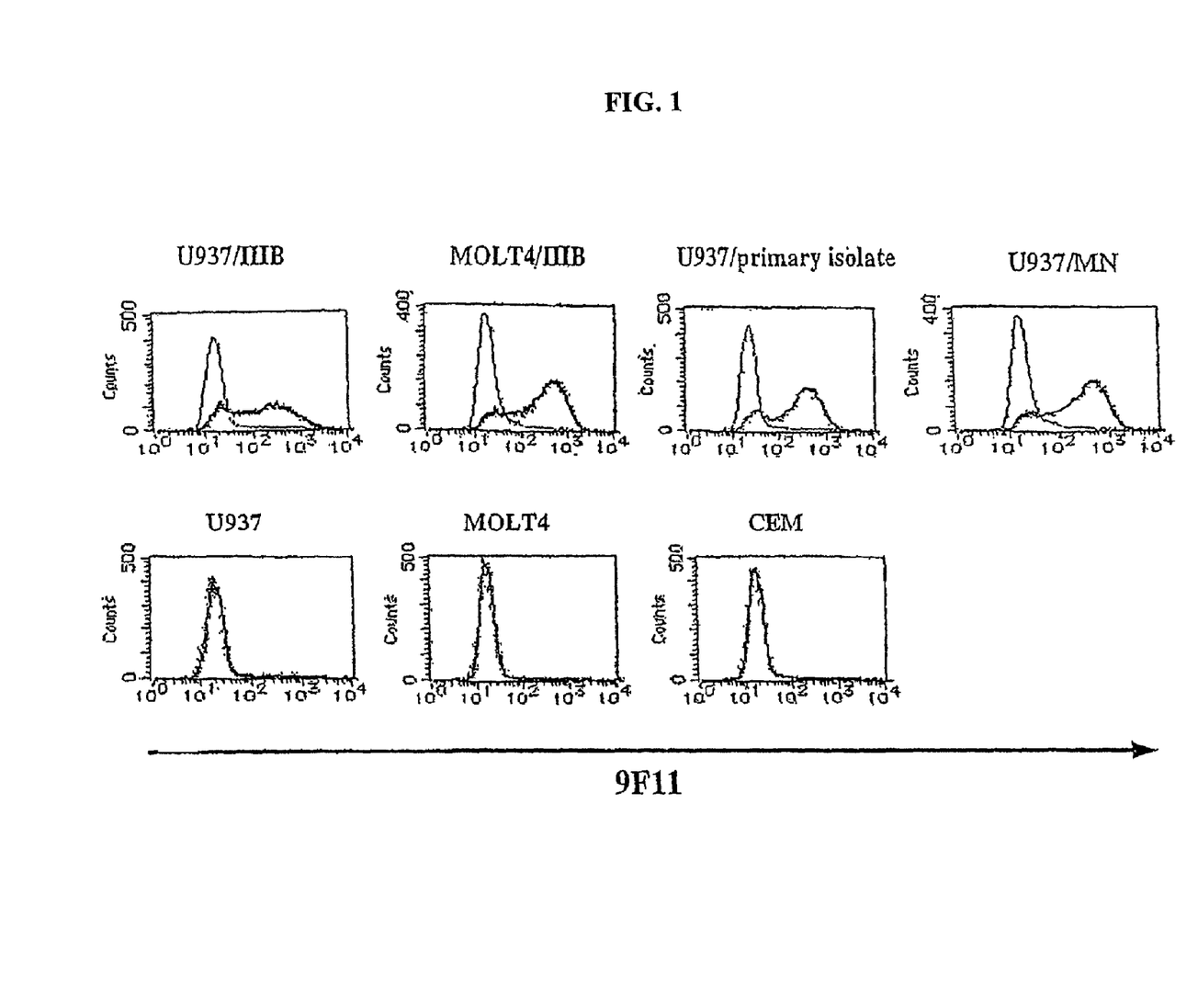
FIG. 1 shows specificity of 9F11 antibody.
Figure 2:
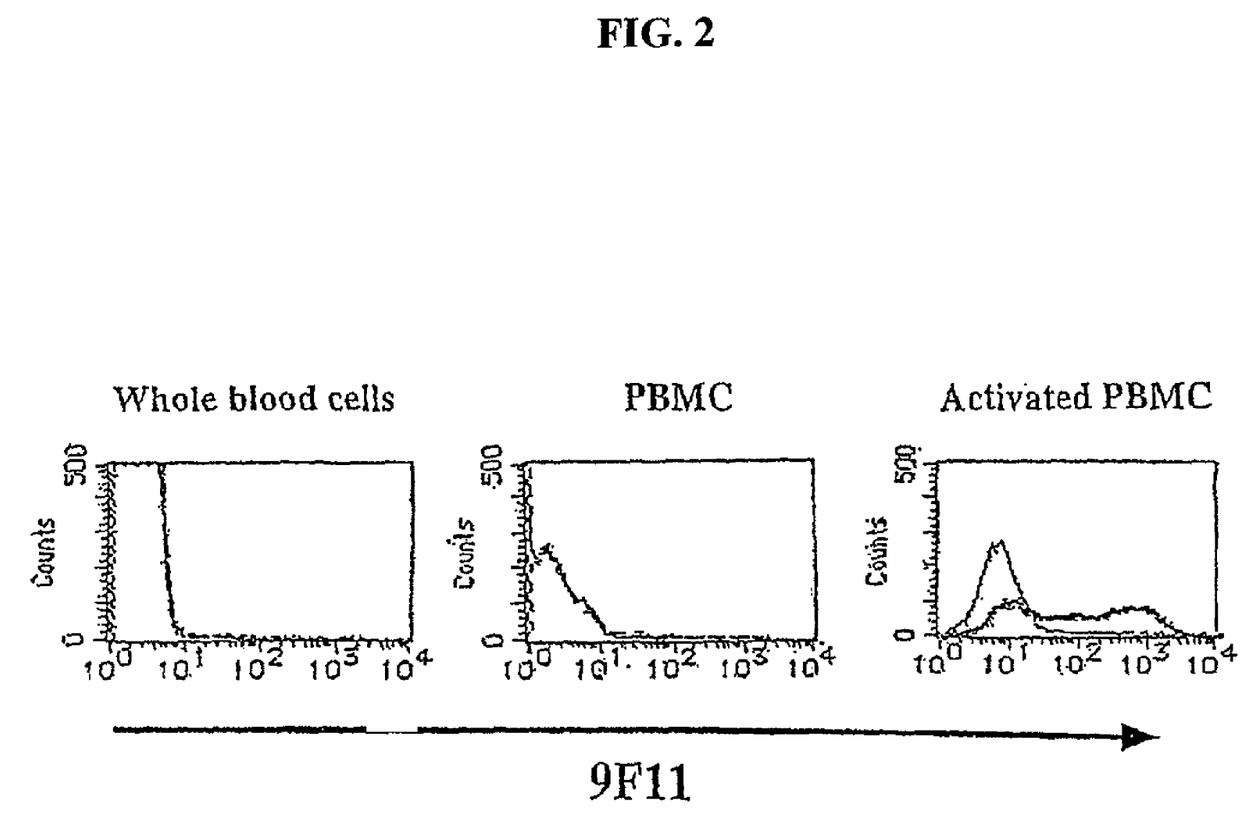
FIG. 2 shows specificity of 9F11 antibody to peripheral blood lymphocytes.

Test cells were suspended in a culture medium in a concentration of $1 \times 10^6$ cells/ml, and an equal volume of a 9F11 antibody solution in a concentration of 10 μg/ml was added to the suspension followed by reacting for 30 minutes. The test cells were washed, linked 9F11 was stained with fluorescence-labeled antihuman IgM antibody, and the cells were analyzed by flow cytometory. The results showed that 9F11 antigen is expressed by HIV infection since, although MOLT-4 cells and CEM cells as human cell strains were not stained, the cells infected with HIV-1 IIIB strain and MN strain were strongly stained (FIG. 1). Since HIV infection induces activation of the lymphocytes, staining of the activated lymphocytes was investigated after cultivating for 3 days by adding phytohemagglutinin (PHA) to the lymphocyte in the peripheral blood cells of a normal person. It was made clear that 9F11 antigen is a differentiated antigen expressed in the activated T-lymphocytes (FIG. 2), since the activated T-lymphocytes stimulated with PHA was strongly stained, although no staining was observed in the peripheral blood cells and peripheral blood lymphocytes not stimulated.

Example 2

Cell Impairing Reaction by 9F11 Antibody Under Mediation by Complement

Figure 3:
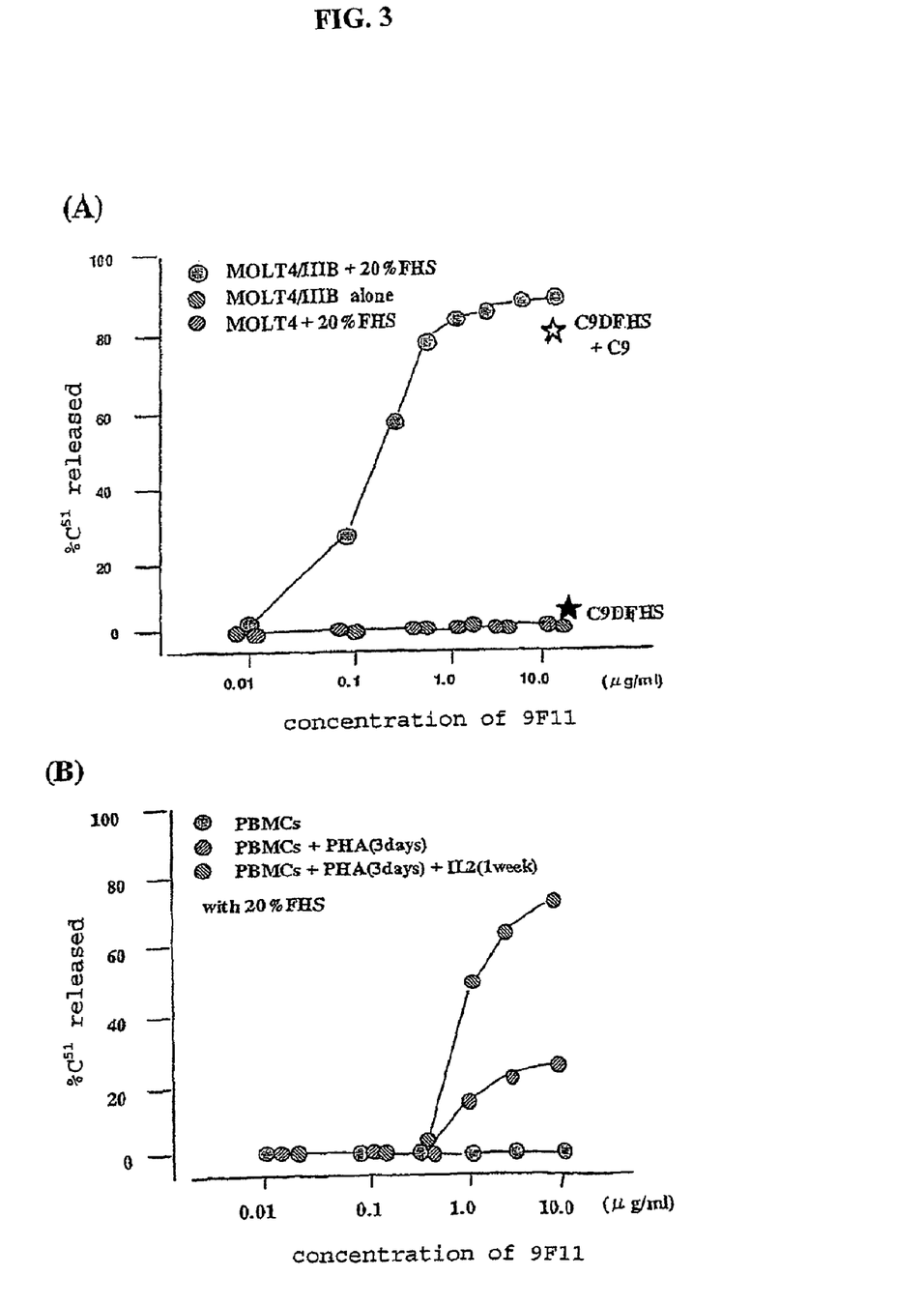
FIG. 3 shows a cell impairing reaction by 9F11 antibody under mediation by the complement.

Test cells were labeled with $^{51}Cr$ as a radioactive isotope in advance, and 40 μl of 9F11 solutions in various concentrations and 20 μl of human fresh serum (complement serum) were added to the labeled test cells (suspended in a culture medium at a concentration of $5 \times 10^5$/ml) to allow the mixture to react for 4 hours on a microtiter plate. After the reaction, the cells were precipitated by centrifugation of the plate, and the radioactivity of $^{51}Cr$ released in the supernatant by cytolysis was measured as an index of the cytolysis reaction. The cells expressing 9F11 antigen such as MOLT-4/IIIB (MOLT-4 cells infected with HIV-1) and peripheral blood derived lymphoblasts activated with PHA were lysed under mediation by the complement in the presence of 2 µg/ml of 9F11. On the contrary, no cytolysis was observed by using an inactivated serum after heating human serum at 56° C. or C9 deficient human fresh serum. Since cytolysis occurs by adding purified C9 to the C9 deficient human fresh serum, it was concluded that the human complement reaction is essential for the cytolysis reaction (FIG. 3).

Example 3

Reconstruction of Antibody by Gene Engineering

An example of the method for reconstruction of 9F11 antibody based on the base sequence of the variable region of 9F11 antibody shown in TABLE 1 will be described below, wherein 9F11 antibody-producing cell strains were established using gene engineering such as a shot-gun ligation method (Grundstrom, T. et al., Nucleic Acid Res. 13, 3305-3316, 1985).

Amino acid sequences of the variable region of 9F11 antibody were obtained by translating the base sequence in the table. There are many base sequences encoding the amino acid sequences in the variable region of 9F11 antibody as shown in Table 2, such as the base sequence of the variable region of original 9F11 antibody as well as those obtained by changing used codons. Base sequences having certain kinds of restriction enzyme recognition fragment were selected from the sequences for every length capable of chemically synthesizing as oligonucleotides (Table 2).

TABLE 2

Examples of cDNA (i.e., SEQ ID NOs: 3 and 4 and conservatively modified variants thereof), encoding the amino acid sequence of 9F11 antibody (SEQ ID NO: 7)

```
1
M   S   V   S   F   L   I   F   L   P   V   L   G   L   P   W   G   V   L   S   SEQ ID NO: 7
ATA TCT GTT TCT TTT TTA ATT TTT TTA CCT GTT TTA GGT TTA CCT TGA GGT GTT TTA TCT SEQ ID NO: 3
ATG TCC GTC TCC TTC TTG ATC TTC TTG CCC GTC TTG GGC TTG CCC TGG GGC GTC TTG TCC SEQ ID NO: 4
    TCA GTA TCA     CTT     CTT CAA GTA CTT GGA CTT CCA     GGA GTA CTT TCA
    TCG GTG TCG     CTC     CTC CCG GTG CTC GGG CTC CCG     GGG GTG CTC TCG
    AGT     AGT     CTA     CTA     CTA     CTA             CTA AGT
    AGC     AGC     CTG     CTG     CTG     CTG             CTG AGC

21
Q   V   Q   L   Q   Q   S   G   P   G   L   V   K   P   A   Q   T   L   S   L
CAA GTT CAA TTA CAA CAA TCT GGT CCT GGT TTA GTT AAA CCT GCT CAA ACT TTA TCT TTA
CAG GTC CAG TTG CAG CAG TCC GGC CCC GGC TTG GTC AAG CCC GCC CAG ACC TTG TCC TTG
    GTA     CTT         TCA GGA CCA GGA CTT GTA     CCA GCA     ACA CTT TCA CTT
    GTG     CTC         TCG GGG CCG GGG CTC GTG     CCG GCG     ACG CTC TCG CTC
            CTA             AGT         CTA                         CTA AGT CTA
            CTG             AGC         CTG                         CTG AGC CTG

41
T   C   A   I   S   G   D   S   V   S   S   N   S   A   T   W   N   W   I   R
ACT TGT GCT ATT TCT GGT GAT TCT GTT TCT TCT AAT TCT GCT ACT TGA AAT TGA ATT CGT
ACC TGC GCC ATC TCC GGC GAC TCC GTC TCC TCC AAC TCC GCC ACC TGG AAC TGG ATC CGC
ACA     GCA     TCA GGA     TCA GTA TCA TCA     TCA GCA ACA                 CGA
ACG     GCG     TCG GGG     TCG GTG TCG TCG     TCG GCG ACG                 CGG
                AGT             AGT AGT AGT     AGT
                AGC             AGC AGC AGC     AGC

61
Q   S   P   L   R   G   L   E   W   L   G   R   T   Y   Y   R   S   K   W   Y
CAA TCT CCT TTA CGT GGT TTA GAA TGA TTA GGT CGT ACT TAT TAT CGT TCT AAA TGA TAT
CAG TCC CCC TTG CGC GGC TTG GAG TGG TTG GGC CGC ACC TAC TAC CGC TCC AAG TGG TAC
    TCA CCA CTT CGA GGA CTT         CTT GGA CGA ACA         CGA TCA
    TCG CCG CTC CGG GGG CTC         CTC GGG CGG ACG         CGG TCG
    AGT     CTA     CTA             CTA                         AGT
    AGC     CTG     CTG             CTG                         AGC

81
N   D   Y   A   V   S   V   K   S   R   I   T   I   N   P   D   T   S   K   N
AAT GAT TAT GCT GTT TCT GTT AAA TCT CGT ATT ACT ATT AAT CCT GAT ACT TCT AAA AAT
AAC GAC TAC GCC GTC TCC GTC AAG TCC CGC ATC ACC ATC AAC CCC GAC ACC TCC AAG AAC
            GCA GTA TCA GTA     TCA CGA     ACA     CCA     ACA TCA
            GCG GTG TCG GTG     TCG CGG     ACG     CCG     ACG TCG
                    AGT             AGT                         AGT
                    AGC             AGC                         AGC

101
Q   F   S   L   Q   L   N   S   V   T   P   E   D   T   A   V   Y   Y   C   A
CAA TTT TCT TTA CAA TTA AAT TCT GTT ACT CCT GAA GAT ACT GCT GTT TAT TAT TGT GCT
CAG TTC TCC TTG CAG TTG AAC TCC GTC ACC CCC GAG GAC ACC GCC GTC TAC TAC TGC GCC
        TCA CTT     CTT     TCA GTA ACA CCA     ACA GCA GTA                 GCA
        TCG CTC     CTC     TCG GTG ACG CCG     ACG GCG GTG                 GCG
        AGT CTA     CTA     AGT
        AGC CTG     CTG     AGC

121
R   E   N   Y   Y   G   S   G   R   Y   N   W   F   D   P   W   G   Q   G   T
CGT GAA AAT TAT TAT GGT TCT GGT CGT TAT AAT TGA TTT GAT CCT TGA GGT CAA GGT ACT
CGC GAG AAC TAC TAC GGC TCC GGC CGC TAC AAC TGG TTC GAC CCC TGG GGC CAG GGC ACC
```

TABLE 2-continued

Examples of cDNA (i.e., SEQ ID NOs: 3 and 4 and conservatively modified variants thereof), encoding the amino acid sequence of 9F11 antibody (SEQ ID NO: 7)

| CGA | GGA TCA GGA CGA | CCA | GGA | GGA ACA |
|-----|-----------------|-----|-----|---------|
| CGG | GGG TCG GGG CGG | CCG | GGG | GGG ACG |
|     | AGT             |     |     |         |
|     | AGC             |     |     |         |
|     |                 | 141 |     |         |
|     |                 | L V T V S S |     |     |
|     |                 | TTA GTT ACT GTT TCT TCT |     |     |
|     |                 | TTG GTC ACC GTC TCC TCC |     |     |
|     |                 | CTT GTA ACA GTA TCA TCA |     |     |
|     |                 | CTC GTG ACG GTG TCG TCG |     |     |
|     |                 | CTA     |     | AGT AGT |
|     |                 | CTG     |     | AGC AGC |

Figure 4:
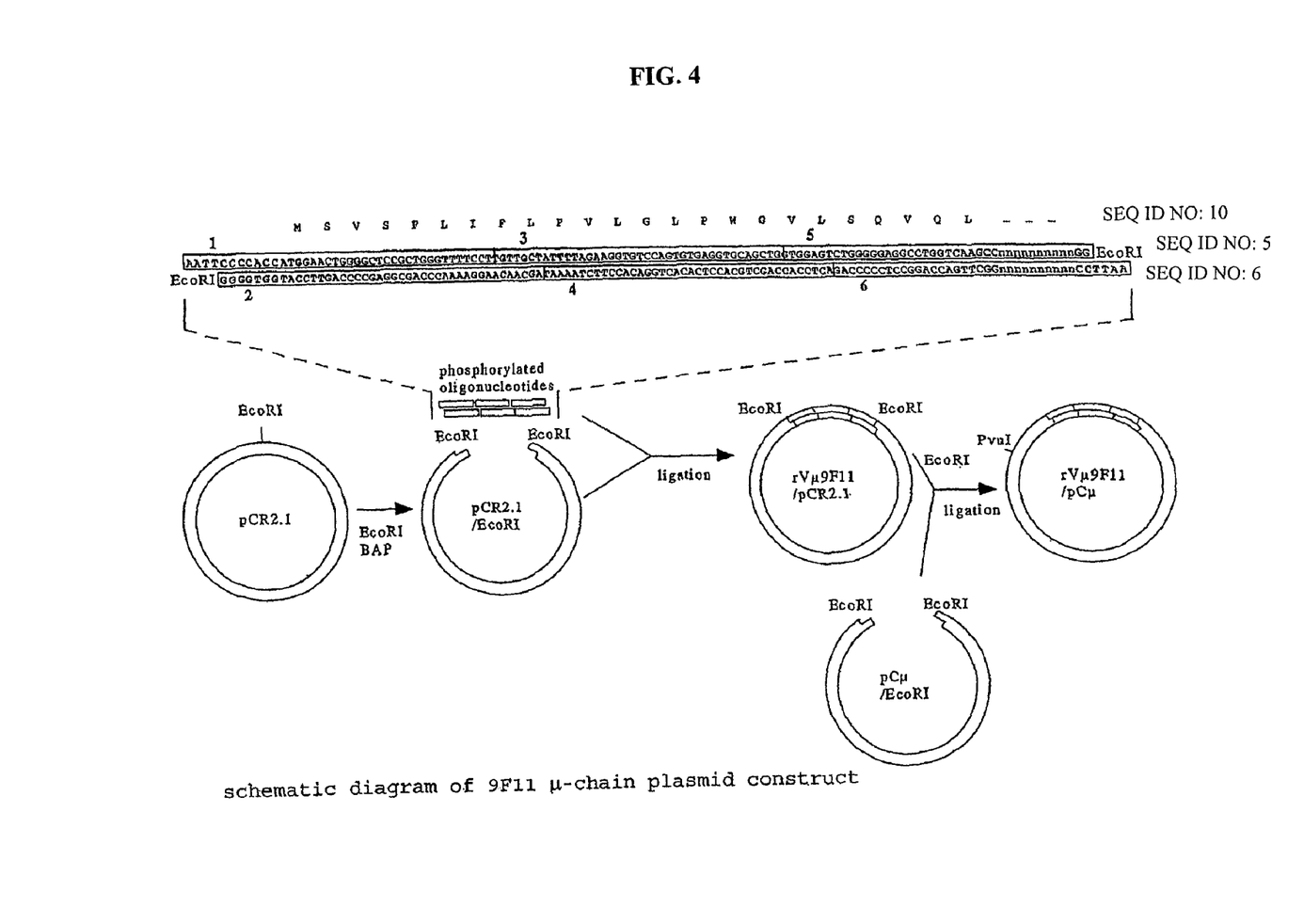
FIG. 4 schematically illustrates 9F11 pt-chain expression plasmid construct.

Oligonucleotides were chemically synthesized based on the base sequence divided for each restriction enzyme-recognition fragment. After sequentially digesting the synthesized oligonucleotide with a corresponding restriction enzyme, a full length of a base sequence encoding the amino acid sequence of the 9F11 antibody variable region by ligation was obtained. cDNA fragments of the 9F11 antibody variable regions of the H-chain and L-chain obtained by the same method with each other (named as rVμ9F11 and rVκ9F11, respectively) were integrated into vectors having constant region gene sequences of H-chain and L-chain of the human IgM antibody (Cμ and Cκ, respectively) by the same method as forming chimera antibodies to obtain recombinant 9F11μ-chain and κ-chain expression plasmids (rVμ9F11-Cμ and rVκ9F11-Cκ, respectively; FIG. 4).

Example 4

Expression of Recombinant Antibody

Activities of the antibodies obtained using the plasmids expressing the reconstructed 9F11 antibody genes were investigated with a temporary expression system in COST cells (ATCC CRL 1651). Genes were introduced using a mixture of two plasmids (rVμ9F11-Cμ and rVκ9F11-Cκ) and an expression plasmid (Cj) for J-chain of human IgM antibody using a lipofectamine reagent according to the protocol by GIBCO Co. Cultivation was continued for two days thereafter under a usual culture condition, and the supernatant of the gene-introduced cell culture was retrieved. Recombinant 9F11 antibodies secreted in the culture supernatant were confirmed by subjecting the culture supernatant to an assay system by the sandwich ELISA method using antihuman μ-antibody and antihuman κ-antibody. The antibodies were confirmed to have specificity as described above by FACS analysis of the culture supernatant using cells such as U937/IIIB and MOLT-4/IIIB prepared by infection of U937 cells and MOLT-4 with IIIB strain of HIV-1. Further, the activity of recombinant 9F11 antibody was confirmed by a competitive inhibition test by allowing fluorescence-labeled original 9F11 antigen and the culture supernatant to simultaneously react with U937/IIIB or MOLT-4/IIIB.

Accordingly, it was confirmed that the base sequences of the μ-chain and κ-chain of 9F11 antibody listed in Table 1 are quite important regions responsible for antibody activity against differentiated antigens of the activated lymphocytes expressed in the HIV-infected cells.

It was also confirmed from these results that genes encoding the base sequences of the μ-chain variable region and κ-chain variable region are quite crucial genes for preparing the recombinant anti-HIV antibody and anti-activated lymphocytes.

INDUSTRIAL APPLICABILITY

Since the human IgM monoclonal antibody of the invention against the differentiated antigens expressed in the activated lymphocytes displays a cytolysis function for the activated lymphocytes under mediation by the complement, the antibody can be used as a remedy for controlling abnormally activated lymphocytes in the body. The invention also provides genes encoding the base sequences of the v chain variable region and x-chain variable regions that are quite crucial for preparing the recombinant anti-activated lymphocytes antibody.

The invention claimed is:

1. A human IgM monoclonal antibody that binds to activated human lymphocytes and HIV-infected cells, wherein said antibody comprises a heavy-chain variable region comprising the amino acid sequence encoded by the nucleotide sequence of SEQ ID NO: 1, and a light-chain variable region comprising the amino acid sequence encoded by the nucleotide sequence of SEQ ID NO: 2.

2. A hybridoma producing a human IgM monoclonal antibody that binds to activated human lymphocytes and HIV-infected cells, wherein said hybridoma is deposited under Accession No. FERM BP-8379.

3. The antibody of claim 1, wherein said antibody is produced by the hybridoma deposited under Accession No. FERM BP-8379.

* * * * *